United States Patent [19]

Furukawa et al.

[11] Patent Number: 5,412,079
[45] Date of Patent: May 2, 1995

[54] LIQUID CRYSTAL MONOMER COMPOUND AND POLYMER OBTAINED THEREFROM

[75] Inventors: Junji Furukawa, Kawasaki; Hiroshi Okamoto, Owariasahi; Yoshio Onouchi, Seto; Takushi Andoh, Fujieda; Satoshi Urano, Tsuzuki, all of Japan

[73] Assignee: Nippon Paint Co., Ltd., Osaka, Japan

[21] Appl. No.: 217,670

[22] Filed: Mar. 25, 1994

[30] Foreign Application Priority Data

Mar. 26, 1993 [JP] Japan .................. 5-067938

[51] Int. Cl.$^6$ ................ C07C 261/00; C09B 29/00
[52] U.S. Cl. .................. 534/732; 534/577; 558/415; 558/416; 558/417; 560/73; 560/164; 526/298; 526/301; 252/299.66; 252/299.67; 252/299.68
[58] Field of Search .......... 560/164, 73; 558/415, 558/416, 417; 534/577, 732

[56] References Cited

U.S. PATENT DOCUMENTS

| | | | |
|---|---|---|---|
| 5,041,509 | 8/1991 | Lee | 526/243 |
| 5,171,803 | 12/1992 | Walton | 526/243 |
| 5,173,381 | 12/1992 | Natansohn | 430/19 |
| 5,187,306 | 2/1993 | Tsubonia | 560/164 |

FOREIGN PATENT DOCUMENTS 0322708 7/1989 European Pat. Off. .
0478268 4/1992 European Pat. Off. .

OTHER PUBLICATIONS

Database WPI, Week 8601, Derwent Publications Ltd., London, GB; AN 86-004325 & JP-A-60 231 642 (Nippon Paint KK), Nov. 18, 1985.
Tanaka, "Polyurethanes Containing An Azobenzene Group In The Side Chain", Makromol. Chem. 189, 771-776 (1988).

Primary Examiner—Michael L. Shippen
Attorney, Agent, or Firm—Wenderoth, Lind & Ponack

[57] ABSTRACT

Disclosed is a liquid crystal monomer compound represented by formula (1):

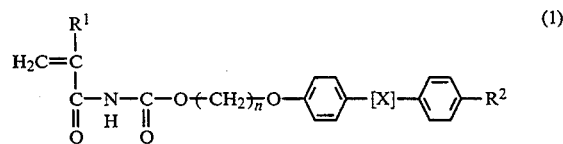

wherein n is an integer of from 2 to 18, X is direct bond, —(C=O)—O—, —(C=O)—NH— or —N=N—, $R^1$ is hydrogen or a lower alkyl group, and $R^2$ is hydrogen, a cyano group or a methoxy group, as well as a liquid crystal polymer derived therefrom.

9 Claims, No Drawings

LIQUID CRYSTAL MONOMER COMPOUND AND POLYMER OBTAINED THEREFROM

FIELD OF THE INVENTION

The present invention relates to a novel liquid crystal monomer compound and a liquid crystal polymer obtained therefrom.

BACKGROUND OF THE INVENTION

Various polymers having liquid crystal characteristics have already been developed. Such polymers generally have the mesogen group represented by formula:

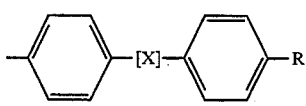

wherein X represents a direct bond, —(C=O)—O—, —(C=O)—NH— or —N=N—, R represents hydrogen, cyano group or methoxy group; present in the polymer backbone (main chain type liquid crystal polymer) or in the side chain (side chain type liquid crystal polymer).

Although the mesogen group shown above is introduced into the polymer via various bonds (e.g. ester bond), few polymers having urethane bond have been reported.

In the main chain type liquid crystal polymer having a higher molecular weight, hydrogen bond characteristics of the urethane bond are considered to serve to bend the terminal of the molecule, whereby reducing the interaction of the mesogen group. Similar tendency is suspected also in the cases of side chain type liquid crystal polymers. Therefore, there are few studies on liquid crystal polymers having urethane bonds in their side chains.

SUMMARY OF THE INVENTION

An objective of the present invention is to provide a side chain type liquid crystal polymer having urethane bonds in the polymer backbone as well as to provide monomer compounds to form such polymers. A liquid crystal polymer having (meth)acrylic main chain and acyl urethane bonds in their side chains is a novel compound.

Accordingly, the present invention provides a liquid crystal monomer compound represented by formula (1):

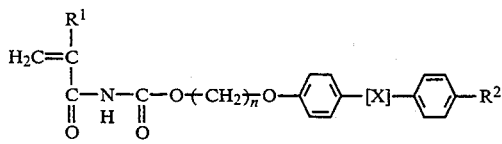

wherein n is an integer of from 2 to 18, X is direct bond, —(C=O)—O—, —(C=O)—NH— or —N=N—, $R^1$ is hydrogen or a lower alkyl group, and $R^2$ is hydrogen, a cyano group or a methoxy group.

The present invention also provides a liquid crystal polymer represented by the formula (2):

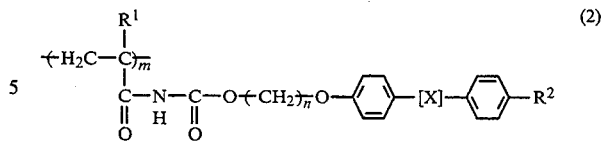

wherein m is an integer of 2 or more, n, X, $R^1$ and $R^2$ are the as mentioned above, as well as a liquid crystal polymer obtained by polymerizing one or more of the liquid crystal monomer compounds represented by formula (1).

DETAILED DESCRIPTION OF THE INVENTION

The monomer compound (1) according to the present invention may be easily synthesized at a high yield by reacting an alkanoyl isocyanate represented by formula (3):

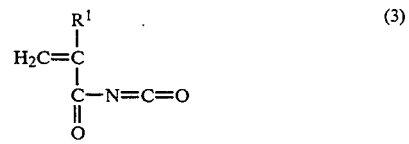

wherein $R^1$ is as defined above, with an active hydrogen containing compound having a mesogen group represented by formula (4):

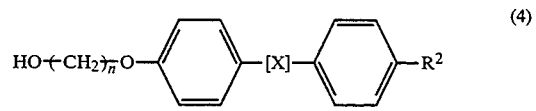

wherein n, X and $R^2$ are defined as above.

The alkanoyl isocyanate (1) has already been provided by the present inventors, and detailed in Japanese Kokai Publication Sho 60(1985)-115557 (corresponding U.S. Pat. No. 4,925,982) and the like. $R^1$ in the alkanoyl isocyanate is hydrogen or a lower alkyl group (preferably having 1 to 4 carbon atoms), with hydrogen and a methyl group being preferred.

The active hydrogen containing compound (4) having mesogen group employed in the present invention is known per se. Generally, the compound (4) can be obtained readily by reaction a biphenyl compound with a compound represented by $Y(CH_2)_nZ$ (wherein Y and Z, same or different, are a halogen atom or an OH group, n=2 to 18), for example α-halogeno-ω-hydroxyalkane, α,ω-dihalogenoalkane or α,ω-dihydroxyalkane (e.g. 2-chloro-1-ethanol).

The reaction between the alkanoyl isocyanate (3) and the active hydrogen compound (4) may be conducted at a temperature of −20° to 100° C. in an inert solvent. An amount ratio of the compound (3) to the compound (4) may be one equivalent of the compound (3) to 0.5 to 1 equivalent of compound (4). The compound obtained was subjected to a standard work up and then purified by, for example, recrystallization. Generally, the obtained product is solid, thus, it is suitable to be recrystallized.

The inert solvents employed in the reaction include aliphatic hydrocarbons such as pentane and hexane; aromatic hydrocarbons such as benzene, toluene and xylene; alicyclic hydrocarbons such as cyclohexane and cyclopentane; halogenated hydrocarbons such as chloroform, dichloromethane, dichlorobenzene and bromobenzene; ketones such as acetone, methyl ethyl ketone and cyclohexanone; esters such as ethyl acetate and butyl acetate; ethers such as diethyl ether, dioxane, diisopropyl ether, THF (tetrahydrofuran), anisole and diphenyl ether; nitriles such as acetonitrile and benzonitrile; amides such as dimethylformamide N-methylpyrrolidone; nitrobenzene; dimethyisulfoxide. The solvent may be selected in view of the solubility of the reactants.

The obtained compound may be polymerized independently by conventional methods such as radical polymerization, or copolymerized using 2 or more monomers, whereby yielding a polymer. The polymerization may be conducted at a temperature of 0° to 150° C. in an inert solvent as listed above in the presence of a polymerization initiator. The polymerization initiator includes an azo initiator such as 2,2′-azobisisobutylonitrile (AIBN) and 2,2′-azobis(2,4-dimethyivaleronitrile); a peroxide initiator such as benzoyl peroxide, di-t-butyl peroxide and t-butyl perbenzoate; and a photopolymerization initiator, such as benzophenone, acetophenone and benzoin.

When liquid crystal characteristics of the polymers obtained as described above has been examined, thermotropic liquid crystal characteristics are found in spite of the presence of the urethane bonds. The liquid crystal monomer compounds according to the present invention may also be employed as a useful reactant for the polymers described above. It is, of course, that the monomer compounds themselves can be used in other applications.

The polymers obtained according to the present invention can be processed and formed into various shapes, such as films, fibers and thin films, in addition to being used as the material for the liquid crystals. They may also be modified widely by employing general modification methods in the field of polymers, such as copolymerization, blending and alloy formation.

EXAMPLES

The present invention is further described in the following examples, which are not intended to limit the present invention.

Reference Example 1

Synthesis of 4-hydroxy-4′-methoxybiphenyl (EBm) from 4,4′-dihydroxybiphenyl 120 ml of water and sodium hydroxide (14.00 g, 0.35 mol) were placed in a conical flask and dissolved. 4,4′-Dihydroxybiphenyl (28.00 g, 0.15 mol) was then added and heated to reflux for 2 hours with stirring using a condenser. Dimethyl sulfate (14.5 ml, 0.15 mol) was added dropwise over about 40 minutes. After addition, the mixture was heated while stirring for 2 hours, and then allowed to cool and filtrated. The filter cake was transferred into 700 ml of water, which was then heated to boiling temperature, and filtrated while still keeping warm. The filtrate was kept at 70° C., and 20% hydrochloric acid was added. White precipitation: formed was washed extensively. Recrystallization from ethanol yielded 4′-methoxy-4-hydroxybiphenyl (13.17 g, Yield: 48.0%).

Reference Example 2

Synthesis of 4′-methoxy-4-hydroxyethoxybiphenyl from 4′-methoxy-4-hydroxybiphenyl 4′-Methoxy-4-hydroxybiphenyl (24.08 g, 0.123 mol) was dissolved in ethanol (180 ml), and aqueous solution (36 ml) of potassium hydroxide (8.36 g, 0.141 mol) was added and heated to reflux for 1 hour. 2-Chloro-1-ethanol (11.96 g, 0.149 mol) was added dropwise over about 30 minutes, and the mixture was heated while stirring at reflux for 23 hours. After the reaction was completed, 180 ml of water was added and ethanol was distilled off. White precipitation formed was filtrated and washed successively with 5% warm aqueous solution of KOH and water, and then dried. Recrystallization from ethanol yielded 4-[2-(N-methacryloyl)carbamoyloxyethoxy]biphenyl.

Reference Examples 3 to 7

The compounds listed below were synthesized similarly as in Reference Examples 1 or 2.

Reference Example 3: 4-hydroxyhexyloxy-4-methoxybiphenyl (HBm)

Reference Example 4: 4-hydroxyethoxybiphenyl (EB)

Reference Example 5: 4-hydroxyhexyloxybiphenyl (HB)

Reference Example 6: 4-hydroxyethoxyazobenzene (EA)

Reference Example 7: 4-hydroxyhexyloxyazobenzene (HA)

In Reference Example 3, 6-chloro-1-hexanol was employed instead of 2-chloro-1-ethanol employed in Reference Example 2, and 4-hydroxybiphenyl was employed in Reference Example 4 instead of 4′-methoxy-4-hydroxybiphenyl employed in Reference example 2. 4-Hydroxybiphenyl and 6-chloro-1-hexanol were employed in Reference Example 5 instead of 4′-methoxy-4-hydroxybiphenyl and 2-chloro-1-ethanol employed in Reference Example 2, respectively. In Reference Examples 6 and 7, azobenzene compounds were: employed instead of biphenyl compounds employed in Reference Examples 4 and 5. Characteristics, melting points and yields of the compounds synthesized are shown in Table 1.

TABLE 1

| Reference example | Compound | n | x | $R^2$ | Melting point (°C.) | Yield (%) |
|---|---|---|---|---|---|---|
| 2 | EBm | 2 | Direct bond | $OCH_3$ | 179.1 | 52.1 |
| 3 | HBm | 6 | Direct bond | $OCH_3$ | 153.5 | 54.1 |
| 4 | EB | 2 | Direct bond | H | 123.5 | 77.5 |
| 5 | HB | 6 | Direct bond | H | 94.0 and 105.9 | 55.8 |
| 6 | EA | 2 | —N=N— | H | 104.5 | 79.1 |
| 7 | HA | 6 | —N=N— | H | 89.3 | 40.2 |

Example 1

EB (1.00 g, $4.7 \times 10^{-3}$ mol) was dissolved in 50 ml of tetrahydrofuran and methacryloyl isocyanate (0.56 g, $5.0 \times 10^{-3}$ mol) was added while cooling to 0° C., and the mixture was stirred for 24 hours. The reaction mixture was poured into 300 ml of water, and the precipitation formed was filtrated and dried. Recrystallization from warm methanol at 40° C. yielded 4-[2-(N-methacryloyl)carbamoyloxyethoxy] biphenyl.

Examples 2 to 6

Except for using HB, EBm, HBm, EA and HA instead of EB employed in Example 1, similar procedure was conducted to obtain the compounds listed below.

UEB: 4-[2-(N-methacryloyl)carbamoyloxyethoxy]-biphenyl
UHB: 4-[6-(N-methacryloyl)carbamoyloxyhexyloxy]-biphenyl
UEBm: 4-[2-(N-methacryloyl)carbamoyloxyethoxy]-4'-methoxybiphenyl
UHBm: 4-[6-(N-methacryloyl)carbamoyloxyhexyloxy]-4'-methoxybiphenyl
UEA: 4-[2-(N-methacryloyl)carbamoyloxyethoxy]azobenzene
UHA: 4-[6-(N-methacryloyl)carbamoyloxyhexyloxy]azobenzene Yields (amounts and rates) and melting points of the compounds obtained are shown in Table 2. Elemental analysis was conducted and the results are shown in Table 3.

TABLE 2

| Example | Compound (I) | Reaction condition (III) $n \times R^2$ g/mol | (IV) $R^1$ g/mol | Temp. °C. | Time h | (I) Yield g | Yield % | Melting point °C. |
|---|---|---|---|---|---|---|---|---|
| 1 | UEB | 2-H $5.05/2.36 \times 10^{-2}$ | $CH_3$ $3.69/2.42 \times 10^{-2}$ | 0 | 24 | 3.77 | 49.2 | 154.7 |
| 2 | UHB | 6-H $4.84/1.79 \times 10^{-2}$ | $CH_3$ $2.28/2.05 \times 10^{-2}$ | 0 | 24 | 4.11 | 60.2 | 84.3 |
| 3 | UEBm | 2-$OCH_3$ $5.26/2.15 \times 10^{-2}$ | $CH_3$ $2.63/2.37 \times 10^{-2}$ | 0 | 24 | 3.36 | 43.9 | 162.4 |
| 4 | UHBm | 6-$OCH_3$ $6.56/2.18 \times 10^{-2}$ | $CH_3$ $2.89/2.60 \times 10^{-2}$ | 0 | 24 | 4.44 | 49.4 | 129.4 |
| 5 | UEA | 2 N=N H $10.02/4.14$ | $CH_3$ $5.04/4.53 \times 10^{-2}$ | 0 | 24 | 6.79 | 46.4 | 152.7 |
| 6 | UHA | 6 N=N H $10.01/3.35 \times 10^{-2}$ | $CH_3$ $4.18/3.76 \times 10^{-2}$ | 0 | 24 | 11.22 | 81.8 | 114.2 |

TABLE 3

| Example No. | Compound | Value of elemental analysis C | H | N | Calculated value C | H | N | Chemical structure |
|---|---|---|---|---|---|---|---|---|
| 1 | UEB | 70.03 | 5.88 | 4.20 | 70.14 | 5.89 | 4.31 | $C_{19}H_{19}NO_4$ |
| 2 | UHB | 72.53 | 7.36 | 3.59 | 72.42 | 7.13 | 3.67 | $C_{23}H_{27}NO_4$ |
| 3 | UEBm | 67.71 | 6.04 | 3.86 | 67.59 | 5.96 | 3.94 | $C_{20}H_{21}NO_5$ |
| 4 | UHBm | 70.14 | 7.05 | 3.33 | 70.05 | 7.10 | 3.40 | $C_{20}H_{29}NO_5$ |
| 5 | UEA | 64.42 | 5.57 | 11.90 | 64.58 | 5.42 | 11.89 | $C_{19}H_{19}N_3O_4$ |
| 6 | UHA | 67.12 | 6.48 | 10.36 | 67.46 | 6.55 | 10.26 | $C_{23}H_{27}N_3O_4$ |

Example 7

UEB (1.0 g, $3.0 \times 10^{-3}$ mol) and azobisisobutyronitrile (0.02 g, $-1.22 \times 10^{-4}$ mol) were dissolved in 1,4-dioxane and polymerization was conducted for 24 hours at 60° C. under argon atmosphere. Then, the reaction mixture was poured into methanol, filtrated to obtain polymer PUEB.

Examples 8 to 12

Except for using UHB, UEB, UHBm, UEA and UHA instead of UEB employed in Example 7, similar procedure was conducted to obtain polymers, whose molecular weights (Mw and Mn) and P (Mw/Mn) are shown in Table 4.

TABLE 4

| Example | Polymer | Mn | Mw | P |
|---|---|---|---|---|
| 7 | PUEB | 5500 | 8500 | 1.55 |
| 8 | PUHB | 12500 | 18000 | 1.44 |
| 9 | PUEBm | 3600 | 6500 | 1.81 |
| 10 | PUHBm | 6000 | 7700 | 1.28 |
| 11 | PUEA | 9000 | 12200 | 1.36 |
| 12 | PUHA | 7600 | 11500 | 1.51 |

Example 13

Polymer PUHB thus obtained was examined by DSC and polarization microscope for its thermodynamic properties and liquid crystal characteristics. As a result, the melting point of the polymer during the course of heating (Tm) and the isotropic fluidization phase transition temperature (Ti) were revealed to be 97.1° C. and 126.6° C., respectively. Examination by a wide angle X-ray diffractometry at room temperature revealed diffraction peaks at $2\Theta = 7.60°$, 19.82° and 23.60°, indicating that the polymer had a high performance as a liquid crystal.

Examples 14 to 18

Similarly to Example 13, the physical parameters of the polymers obtained in Examples 7 and 9 to 12 were examined, and the results are shown in Table 5.

TABLE 5

| Example | Polymer | Phase transition temperature (°C.) Tm | Ti | Transition enthalpy (J/g) ΔHM | ΔHi |
|---|---|---|---|---|---|
| 13 | PUEB | | 136.4 | | 19.54 |
| 14 | PUHB | 97.1 | 126.6 | 8.25 | 25.45 |
| 15 | PUEBm | 139.7 | 156.6 | 10.70 | 33.15 |
| 16 | PUHBm | | 136.3 | | |
| 17 | PUEA | 128.7 | 140.3 | 7.7 | 4.13 |
| 18 | PUHA | | (126.7) | | 44.58 |

What is claimed is:

1. A liquid crystal monomer compound represented by formula (1):

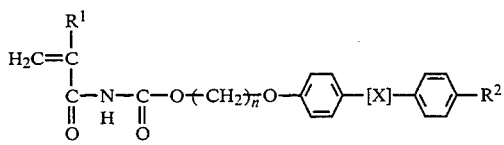

wherein n is an integer of from 2 to 18, X is direct bond, —(C=O)—O—, —(C=O)—NH— or —N=N—, $R^1$ is hydrogen or a lower alkyl group, and $R^2$ is hydrogen, a cyano group or a methoxy group.

2. A liquid crystal monomer according to claim 1 wherein X is direct bond or —N=N—, $R^1$ is methyl, $R^2$ is hydrogen, a cyano group or a methoxy group.

3. A liquid crystal monomer according to claim 1 wherein $R^1$ is a hydrogen atom or a methyl group.

4. A liquid crystal monomer according to claim 1 being 4-[2-(N-methacryloyl)carbamoyloxyethoxy] biphenyl.

5. A liquid crystal monomer according to claim 1 being 4-[6-(N-methacryloyl)carbamoyloxyhexyloxy] biphenyl.

6. A liquid crystal monomer according to claim 1 being 4-[2-(N-methacryloyl)carbamoyloxyethoxy]-4'-methoxy biphenyl.

7. A liquid crystal monomer according to claim 1 being 4-[6-(N-methacryloyl)carbamoyloxyhexyloxy]-4'-methoxy biphenyl.

8. A liquid crystal monomer according to claim 1 being 4-[2-(N-methacryloyl)carbamoyloxyethoxy]azobenzene.

9. A liquid crystal monomer according to claim 1 being 4-[6-(N-methacryloyl)carbamoyloxyhexyloxy]azobenzene.

* * * * *